United States Patent [19]

Abe et al.

[11] Patent Number: 5,703,272
[45] Date of Patent: Dec. 30, 1997

[54] PROCESS FOR PREPARING A CARBOXYLIC ACID ESTER

[75] Inventors: Mariko Abe; Shuji Ebata; Takafumi Abe; Hirofumi Higuchi, all of Niigata, Japan

[73] Assignee: Mitsubishi Gas Chemical Company, Inc., Tokyo, Japan

[21] Appl. No.: 707,135

[22] Filed: Sep. 3, 1996

Related U.S. Application Data

[62] Division of Ser. No. 366,812, Dec. 30, 1994, Pat. No. 5,587,349.

[30] Foreign Application Priority Data

Feb. 15, 1994 [JP] Japan .......................... 6-18341

[51] Int. Cl.⁶ ............................................. C07C 69/02
[52] U.S. Cl. .................... 560/231; 560/8; 560/106; 560/129; 560/190; 560/205; 560/221; 560/254
[58] Field of Search .................... 560/231, 205, 560/8, 106, 221, 254, 129, 190

[56] References Cited

U.S. PATENT DOCUMENTS

| | | |
|---|---|---|
| 4,018,816 | 4/1977 | Onoda et al. . |
| 4,176,089 | 11/1979 | Cull . |
| 4,547,557 | 10/1985 | McDaniel . |
| 4,981,831 | 1/1991 | Knudsen et al. .......... 502/242 |
| 5,162,283 | 11/1992 | Moini . |
| 5,189,201 | 2/1993 | Sano et al. .............. 560/205 |
| 5,587,349 | 12/1996 | Abe et al. ............... 502/236 |

FOREIGN PATENT DOCUMENTS 2436  1/1978  Japan .

*Primary Examiner*—Wayne Langel
*Attorney, Agent, or Firm*—Frishauf, Holtz, Goodman, Langer & Chick, P.C.

[57] ABSTRACT

A process for preparing a carboxylic acid ester which includes subjecting a carboxylic acid and an alcohol or a phenol to an esterification reaction in the presence of a silica-titania catalyst. The silica-titania catalyst is prepared by adding an acidic solution containing a silicon compound and a titanium compound dissolved therein to a solution of a basic compound to bring about co-precipitation, in which the acidic solution is a nitric acid-acidic solution or a sulfuric acid-acidic solution, a ratio of the amount (gram equivalent) of nitric acid or sulfuric acid to the amount (mol) of the silicon compound in the acidic solution is 0.5 to 50 and the amount of the titanium compound in the acidic solution is such that a ratio of titania ($TiO_2$) in the silica-titania catalyst is 1 to 50% by weight.

14 Claims, No Drawings

PROCESS FOR PREPARING A CARBOXYLIC ACID ESTER

This is a division of application Ser. No. 08/366,812 filed Dec. 30, 1994, which issued as U.S. Pat. No. 5,587,349.

BACKGROUND OF THE INVENTION

1. Field of the Invention

The present invention relates to a process for preparing a silica-titania catalyst, and more specifically, it relates to a process for preparing a silica-titania solid acid catalyst for use in various kinds of industrially useful esterification reactions.

2. Description of the Related Art

Silica-titania catalysts (hereinafter referred to sometimes as "silica-titania solid acid catalysts") have been manufactured by usual preparation methods for solid catalysts such as an impregnating method, a kneading method, a co-precipitation method and a sol-gel method.

The above-mentioned co-precipitation method comprises dissolving a silicon compound and a titanium compound, and then adjusting the pH of the mixture to co-precipitate the silicon compound and the titanium compound. In the preparation of the silica-titania catalyst by this method, the silicon compound and the titanium compound which are relatively inexpensive can be used as starting materials, and the preparation of the catalyst is relatively easy. For these reasons, the co-precipitation method has often been industrially been employed.

However, in the case that the silica-titania prepared by the conventional co-precipitation method is used as a catalyst for an esterification reaction or the like, its activity is low, and for this reason, this kind of silica-titania catalyst is not satisfactory for an industrial use. In order to improve the catalytic activity, Japanese Patent Publication No. 53418/1981 has suggested a method in which a crystalline cellulose is used as a precipitation auxiliary for the silicon compound and the titanium compound. However, this method requires the use of a large amount of the crystalline cellulose, which leads to a low volume efficiency at the time of the catalyst preparation and a high manufacturing cost, and in addition, the activity of the obtained silica-titania catalyst is not so high. In consequence, the thus obtained catalyst is not satisfactory as the industrial solid acid catalyst for the esterification reaction or the like.

SUMMARY OF THE INVENTION

The present inventors have intensively investigated with the intention of developing a highly active silica-titania catalyst by which the drawbacks of the above-mentioned conventional methods can be overcome. As a result, it has been found that an object of the present invention can be achieved by co-precipitating a silicon compound and a titanium compound in a highly concentrated acidic solution of nitric acid or sulfuric acid. The present invention has been completed on the basis of this knowledge.

That is to say, according to the present invention, there is provided a process for preparing a silica-titania catalyst by adding an acidic solution containing a silicon compound and a titanium compound dissolved therein to a solution of a basic compound to bring about co-precipitation, in which the acidic solution is a nitric acid-acidic or a sulfuric acid-acidic solution; a ratio of the amount (gram equivalent) of nitric acid or sulfuric acid to the amount (mol) of the silicon compound in the acidic-solution is in the range of 0.5 to 50; and the amount of the titanium compound in the acidic solution is such that a ratio of titania ($TiO_2$) in the silica-titania catalyst to be prepared is in the range of 1 to 50% by weight.

According to the process of the present invention, the highly active silica-titania solid acid catalyst suitable for an esterification reaction and the like can efficiently be prepared.

DESCRIPTION OF THE PREFERRED EMBODIMENTS

Next, a process of the present invention will be described in detail.

In order to prepare a silica-titania solid acid catalyst by the process of the present invention, a silicon compound can be used as a material, and examples of the silicon compound includes various kinds of compounds, but typical examples of the silicon compound usually include ethyl orthosilicate, silicon tetrachloride, water glass and sodium silicate. Each of these silicon compounds is used in a condition where it is dissolved in water, an acid or a water-alcohol mixing solvent. Of the above-mentioned examples, sodium silicate is particularly preferable from the viewpoints of handling and economy.

As another material, a titanium compound is also used, and examples of the titanium compound include various kinds of compounds. Typical examples of the titanium compound usually include titanium sulfate, titanium oxysulfate, titanium nitrate, titanium tetrachloride and orthotitanates. Each of these titanium compounds is used in a condition where it is dissolved in water, an acid or a water-alcohol mixing solvent. Of the above-mentioned examples, titanium sulfate, titanium oxysulfate and titanium nitrate are particularly preferable.

A weight ratio between the silicon compound and the titanium compound in the process of the present invention is suitably decided in compliance with use and purpose. However, in the case of the solid acid catalyst for an esterification reaction or the like, a ratio of titania ($TiO_2$) in silica-titania is usually in the range of 1 to 50% by weight, preferably 5 to 40% by weight, and therefore, the silicon compound and the titanium compound are used in a weight ratio corresponding to this ratio. That is to say, the amount of the titanium compound in the acidic solution in which the silicon compound and the titanium compound are dissolved is selected so that the ratio of titania ($TiO_2$) in the silica-titania catalyst to be prepared is in the range of 1 to 50% by weight, preferably 5 to 40% by weight.

In the preparation of the silica-titania catalyst by the co-precipitation method, an acid is used, and examples of the acid include strong acids, for example, mineral acids such as sulfuric acid, hydrochloric acid and nitric acid, and organic sulfonic acids such as methanesulfonic acid and p-toluenesulfonic acid. However, as an acid which can be used in the process of the present invention, nitric acid and sulfuric acid are most preferable, because these acids are economical, can provide an excellent catalyst performance and a sufficient acid strength, and can facilitate post-treatments such as water washing and calcination after the co-precipitation.

When the concentration of the acid for use in the process of the present invention is increased, the activity of the obtained catalyst can be improved. This is to say, when the concentration of the acid is increased, a gelation rate increases at the time of the co-precipitation, so that the dispersibility of both the silicon compound and the titanium compound heightens and a specific surface area of the prepared silica-titania also increases. Furthermore, when the concentration of the acid is increased, an effect of removing alkaline components derived from a silicon compound such as sodium silicate enhances, so that the amount of the acid as the solid acid of the produced silica-titania increases. Thus, it can be considered that the improvement of the activity as the solid acid catalyst in the esterification reaction is due to a synergistic effect of these functions.

As understood from the foregoing, the larger the amount of the acid to be used is, the higher the catalytic activity of the silica-titania is. However, if the amount of the acid is in excess of a certain level, the activity of the catalyst is not improved any more, so that a larger amount of a basic substance is required to adjust a pH of the acidic solution, which is not practical. In view of this point, in the method of the present invention, a ratio of the amount (gram equivalent) of nitric acid or sulfuric acid to the amount (mol) of the silicon compound, i.e., the nitric acid amount or the sulfuric acid amount (gram equivalent)/the silicon compound amount (mol) is in the range of 0.5 to 50, preferably 1.0 to 20. Here, the gram equivalent means a valency×mols of the acid. Therefore, if the ratio of the acid to the silicon compound is converted into a molar ratio, the molar ratio of nitric acid to the silicon compound is in the range of 0.5 to 50, and the molar ratio of sulfuric acid to the silicon compound is in the range of 0.25 to 25.

Furthermore, no particular restriction is put on the amount of water which can be used to prepare the acidic solution, but a minimum amount necessary to dissolve the silicon compound and the titanium compound is enough.

In the method of the present invention, a basic compound is used, and this basic compound usually is a basic compound which can be used to neutralize the aqueous acidic solution. Typical examples of the basic compound include ammonia, ammonium carbonate, ammonium bicarbonate, urea, alkali metal hydroxides, alkali metal carbonates and aqueous solutions thereof, but ammonia, an ammonium salt such as ammonium bicarbonate and aqueous solutions thereof are preferable, because these basic compounds can provide an excellent catalyst performance, can easily be handled at the time of the catalyst preparation, can easily be decomposed and removed by calcination, and are economical.

In the present invention, no particular restriction is put on a manner of mixing the basic compound with the aqueous acidic solution containing the silicon compound and the titanium compound dissolved therein. After the mixing, it is preferable to carry out aging, and this aging is preferably done in the temperature range of 20° to 110° C., more preferably 30° to 100° C. It is also effective to adjust a pH of the solution by adding a buffer solution, if necessary.

By this mixing of the acidic solution with the basic compound, a co-precipitate can be obtained, and this co-precipitate, i.e., the hydrogel-like silicon and titanium compound is filtered, washed, dried and then calcined in accordance with a usual manner to obtain the desired silica-titania solid acid catalyst.

At this time, a calcination temperature is preferably in the range of 200° to 1000° C., more preferably 250° to 600° C., and the calcination is carried out in air or in the presence of an oxygen gas diluted with an inert gas in an optional ratio.

The silica-titania catalyst obtained by the method of the present invention is useful as the catalyst for various organic reactions, and in particular, this catalyst is extremely highly active to an esterification reaction of a carboxylic acid and an alcohol or a phenol and is excellent in selectivity. Therefore, the employment of this silica-titania catalyst permits effectively preparing a desired carboxylic acid ester.

Examples of the material carboxylic acid for the esterification reaction to which the catalyst of the present invention can be applied include saturated and unsaturated aliphatic carboxylic acids such as acetic acid, propionic acid, butyric acid, isobutyric acid, acrylic acid, methacrylic acid and adipic acid, and aromatic carboxylic acids such as benzoic acid and terephthalic acid.

On the other hand, examples of the aforesaid alcohol include saturated and unsaturated aliphatic alcohols such as methanol, ethanol, propanol, isopropanol, butanol, isobutanol, ethylene glycol, butanediol and allyl alcohol. In addition, phenols such as phenol and p-methylphenol can also be used in place of the alcohols.

The catalyst obtained by the process of the present invention similarly exerts a high activity and a selectivity to an ester hydrolysis reaction and an ester exchange reaction which are reactions similar to the esterification reaction.

Examples of a material for the ester hydrolysis reaction and the ester exchange reaction to which the catalyst of the present invention can be applied include esters comprising combinations of the carboxylic acids and the alcohols or the phenols usable in the above-mentioned esterification reaction.

With regard to a reaction morphology in which the catalyst of the present invention is used, a gaseous phase and a liquid phase are acceptable, and from the viewpoint of a reaction rate, the catalyst can be particularly advantageously used in the gaseous phase. In particular, in the case that an unstable material such as methacrylic acid, acrylic acid, allyl alcohol or methyl methacrylate is used, a good effect can be obtained in the gaseous phase in which a high conversion ratio can be achieved, even if a contact time with the catalyst is short. With regard to a reaction system, a suspension process or a fixed bed system is preferable in the liquid phase reaction, and the fixed bed system is preferable in the gaseous phase reaction.

The reaction temperature is usually in the range of from room temperature to 450° C., preferably 60° to 400° C. and particularly in the case of the gaseous phase reaction, the reaction temperature is suitably selected in the range of 120° to 360° C. In the case that the gaseous phase reaction is carried out, the materials may be diluted with nitrogen, air or a carbon dioxide gas which is a gas substantially inert to the reaction.

The high activity of the catalyst of the present invention can stably be maintained for a long term, but if the activity of the catalyst has deteriorated, this activity can easily be recovered by calcining the catalyst in the presence of an oxygen-containing gas such as air.

As described above, a silica-titania catalyst prepared at a high acid concentration by a co-precipitation method in accordance with a process of the present invention can exert an excellent catalytic activity for an esterification reaction and the like, and the industrial value of the silica-titania catalyst is very high.

Next, the present invention will be described in detail with reference to examples and comparative examples, but the scope of the present invention should not be limited to these examples.

EXAMPLE 1

(Preparation of catalyst-1)

In a 500-ml beaker were placed 16.6 g of concentrated nitric acid (60% by weight), 20.9 g ($HNO_3$/Si molar ratio=

1.6) of sodium silicate (No. 3) and 2.8 g of titanium sulfate [Ti(SO$_4$)$_2$.H$_2$O], and they were dissolved in 150 ml of water at 40° C. by stirring. The resulting solution was poured at 40° C. into a 1-liter beaker containing a solution obtained by dissolving 12.5 g of ammonium bicarbonate in 200 ml of water under stirring.

Afterward, the solution was heated up to 60° C., and stirred for 2 hours to age the resulting precipitate. Next, after being cooled to room temperature, the precipitate was filtered with suction, and then sufficiently washed with water. The resulting precipitate was dried at 110° C., and then calcined at 500° C. for 3 hours in air.

After the calcination, 6.6 g of white silica-titania was obtained in the state of small masses.

The thus obtained silica-titania was subjected to fluorescent X-ray analysis, and as a result, it was apparent that a TiO$_2$ component content was 13% by weight and an Na content was 0.63%. In addition, the specific surface area of the silica-titania measured by an adsorption method was 558 m$^2$/g, and an acid content (H$_0 \leq$1.5) measured by an amine titration method using a Hammett indicator was 0.49 mmol/g.

EXAMPLE 2

(Preparation of catalyst-2)

The same procedure as in Example 1 was carried out except that 33.2 g of concentrated nitric acid was used and ammonium bicarbonate was replaced with 20.2 g (HNO$_3$/Si molar ratio=3.2) of 28% by weight aqueous ammonia. The yield of silica-titania was 6.5 g, a TiO$_2$ component content was 13% by weight, an Na content was 0.24%, a specific surface area was 571 m$^2$/g, and an acid content (H$_0 \leq$1.5) was 0.55 mmol/g.

EXAMPLE 3

(Preparation of catalyst-3)

The same procedure as in Example 1 was carried out except that 63.0 g of concentrated nitric acid and 51.3 g of ammonium bicarbonate (HNO$_3$/Si molar ratio=6.1) were used.

The yield of silica-titania was 6.3 g, a TiO$_2$ component content was 13% by weight, an Na content was 0.11%, a specific surface area was 560 m$_2$/g, and an acid content (H$_0 \leq$1.5) was 0.50 mmol/g.

COMPARATIVE EXAMPLE 1

(Preparation of catalyst-11)

In a 500-ml beaker were placed 1.59 g of concentrated sulfuric acid (97% by weight), 20.9 g of sodium silicate (No. 3) (H$_2$SO$_4$/Si molar ratio=0.16) and 2.8 g of titanium sulfate [Ti(SO$_4$)$_2$.H$_2$O], and they were dissolved in 150 ml of water by stirring at 40° C. Afterward, 1.74 g of a crystalline cellulose powder (fine powder Abicel FE-F20 made by Asahi Chemical Industry Co., Ltd.) was added thereto. The resulting solution was then poured at 40° C. into a 1-liter beaker containing a solution obtained by dissolving 1.0 g of ammonium bicarbonate in 200 ml of water under stirring.

Afterward, the solution was heated up to 60° C., and stirred for 2 hours to age the resulting precipitate. Next, after being cooled to room temperature, the precipitate was filtered with suction, and then sufficiently washed with water. The resulting precipitate was dried at 110° C., and then calcined at 500° C. for 3 hours in air.

After the calcination, 6.6 g of white silica-titania was obtained in the state of small masses.

The thus obtained silica-titania was subjected to fluorescent X-ray analysis, and as a result, a TiO$_2$ component content was 13% by weight and an Na content was 1.90%. In addition, a specific surface area measured by an adsorption method was 510 m$^2$/g, and an acid content (H$_0 \leq$1.5) measured by an amine titration method using a Hammett indicator was 0.33 mmol/g.

COMPARATIVE EXAMPLE 2

(Preparation of catalyst-12)

The same procedure as in Example 1 was carried out except that 3.3 g of concentrated nitric acid and 1.0 g of ammonium bicarbonate (HNO$_3$/Si molar ratio=0.32) were used.

The yield of silica-titania was 6.7 g, a TiO$_2$ component content was 13% by weight, an Na content was 1.92%, a specific surface area was 495 m$^2$/g, and an acid content (H$_0 \leq$1.5) was 0.34 mmol/g.

EXAMPLE 4

(Preparation of catalyst-4)

The same procedure as in Example 1 was carried out except that 1.0 g of titanium sulfate and 9.8 g of ammonium bicarbonate were used.

The yield of silica-titania was 6.1 g, a TiO$_2$ component content was 5% by weight, and a specific surface area was 566 m$^2$/g.

EXAMPLE 5

(Preparation of catalyst-5)

The same procedure as in Example 1 was carried out except that 12.9 g of titanium sulfate and 25.9 g of ammonium bicarbonate were used.

The yield of silica-titania was 9.6 g, a TiO$_2$ component content was 40% by weight, and a specific surface area was 463 m$^2$/g.

EXAMPLE 6

(Preparation of catalyst-6)

The same procedure as in Example 1 was carried out except that 7.99 g of concentrated sulfuric acid having a concentration of 97% (H$_2$SO$_4$/Si molar ratio=0.8) was used in place of concentrated nitric acid.

The yield of silica-titania was 6.5 g, a TiO$_2$ component content was 13% by weight, an Na content was 0.65%, a specific surface area was 553 m$^2$/g, and an acid content (H$_0 \leq$1.5) was 0.48 mmol/g.

EXAMPLE 7

(Preparation of catalyst-7)

The same procedure as in Example 1 was carried out except that 8.2 g of concentrated nitric acid and 5.2 g of ammonium bicarbonate (HNO$_3$/Si molar ratio=0.80) were used.

The yield of silica-titania was 6.5 g, a TiO$_2$ component content was 13% by weight, an Na content was 1.01%, a specific surface area was 539 m$^2$/g, and an acid content (H$_0 \leq$1.5) was 0.37 mmol/g.

COMPARATIVE EXAMPLE 3

(Preparation of catalyst-13)

The same procedure as in Example 1 was carried out except that 46.8 g of titanium sulfate and 71.6 g of ammonium bicarbonate were used. The yield of silica-titania was 19.6 g, a $TiO_2$ component content was 70% by weight, and a specific surface area was 320 m²/g.

COMPARATIVE EXAMPLE 4

(Preparation of catalyst-14)

The same procedure as in Example 1 was carried out except that no titanium sulfate was added and 8.4 g of ammonium bicarbonate was used.

The yield of silica was 5.8 g, and a specific surface area was 392 m²/g.

REACTION EXAMPLE 1

First, 1.5 g of a catalyst 11 (10–20 mesh) was placed in a pyrex glass reactor (internal diameter=10 mm), and a mixture having a composition of methacrylic acid/methyl methacrylate/methanol=1/9/20 (molar ratio) was introduced thereinto at a feed rate of 2.0 g/hour by the use of a microfeeder. Then, reaction was carried out at 150° C. under atmospheric pressure.

The resulting reaction product was cooled, and the thus condensed solution was then analyzed by gas chromatography. As a result, the conversion of methacrylic acid was 42%, 20 hours after the start of the reaction, and that of methacrylic acid was 30%, 168 hours after the start of the reaction.

REACTION EXAMPLE 2

Following the same procedure as in Reaction Example 1 except that a catalyst 11 was replaced with catalysts 1 to 3 and catalysts 7 and 12, a continuous gaseous phase esterification reaction of methacrylic acid and methanol was carried out.

The results are shown in Table 1.

TABLE 1

| Catalyst | Preparation Procedure | Conversion (%) of Methacrylic Acid | |
|---|---|---|---|
| | | after 20 hours | after 168 hours |
| Catalyst 12 | Comp. Ex. 2 | 36 | 22 |
| Catalyst 1 | Example 1 | 66 | 59 |
| Catalyst 2 | Example 2 | 68 | 59 |
| Catalyst 3 | Example 3 | 69 | 60 |
| Catalyst 7 | Example 7 | 52 | 43 |

REACTION EXAMPLE 3

Following the same procedure as in Reaction Example 1 except that a catalyst 11 was replaced with catalysts 4 and 5 and catalysts 13 and 14, a continuous gaseous phase esterification reaction of methacrylic acid and methanol was carried out.

The results are shown together with the results of a catalyst 1 in Table 2.

TABLE 2

| Catalyst | Preparation Procedure | $TiO_2$ Content (wt%) | Conversion (%) of Methacrylic Acid |
|---|---|---|---|
| Catalyst 13 | Comp. Ex. 3 | 70 | 21 |
| Catalyst 14 | Comp. Ex. 4 | 0 | 8 |
| Catalyst 1 | Example 1 | 13 | 66 |
| Catalyst 4 | Example 4 | 5 | 58 |
| Catalyst 5 | Example 5 | 40 | 53 |

REACTION EXAMPLE 4

Following the same procedure as in Reaction Example 1 except that a catalyst 11 was replaced with a catalyst 6, a continuous gaseous phase esterification reaction of methacrylic acid and methanol was carried out. As a result, the conversion of methacrylic acid was 65%, 20 hours after the start of the reaction.

What is claimed is:

1. A process for preparing a carboxylic acid ester which comprises subjecting a carboxylic acid and an alcohol or a phenol to an esterification reaction in the presence of a silica-titania catalyst, the silica-titania catalyst having been prepared by a process comprising adding an acidic solution containing a silicon compound and a titanium compound dissolved therein to a solution of a basic compound to bring about co-precipitation, wherein the acidic solution is a nitric acid-acidic solution or a sulfuric acid-acidic solution; a ratio of the amount (gram equivalent) of nitric acid or sulfuric acid to the amount (mol) of the silicon compound in the acidic solution is 0.5 to 50; and the amount of the titanium compound in the acidic solution is such that a ratio of titania ($TiO_2$) in the silica-titania catalyst is 1 to 50% by weight.

2. The process for preparing a carboxylic acid ester according to claim 1, wherein the silicon compound is sodium silicate.

3. The process for preparing a carboxylic acid ester according to claim 1, wherein the titanium compound is at least one compound selected from the group consisting of titanium sulfate, titanium oxysulfate, titanium nitrate and titanium tetrachloride.

4. The process for preparing a carboxylic acid ester according to claim 1, wherein the basic compound is at least one compound selected from the group consisting of ammonia and ammonium salt.

5. The process for preparing a carboxylic acid ester according to claim 1, wherein the ratio of the amount (gram equivalent) of nitric acid or sulfuric acid to the amount (mol) of the silicon compound in the acidic solution is 1 to 20.

6. The process for preparing a carboxylic acid ester according to claim 1, wherein the amount of the titanium compound in the acidic solution is such that a ratio of titania ($TiO_2$) in the silica-titania catalyst is 5 to 40% by weight.

7. The process for preparing a carboxylic acid ester according to claim 1, wherein the carboxylic acid is methacrylic acid and the alcohol is methanol.

8. The process for preparing a carboxylic acid ester according to claim 7, wherein the carboxylic acid is selected from the group consisting of acetic acid, propionic acid, butyric acid, isobutyric acid, acrylic acid, methacrylic acid, adipic acid, benzoic acid and terephthalic acid.

9. The process for preparing a carboxylic acid ester according to claim 8, wherein the carboxylic acid is reacted with an alcohol, said alcohol being selected from the group consisting of methanol, ethanol, propanol, isopropanol, butanol, isobutanol, ethylene glycol, butanediol and allyl alcohol.

10. The process for preparing a carboxylic acid ester according to claim 8, wherein the carboxylic acid is reacted with a phenol, said phenol being selected from the group consisting of phenol and p-methylphenol.

11. The process for preparing a carboxylic acid ester according to claim 9, wherein the process is carried out at a temperature of 120° to 360° C.

12. The process for preparing a carboxylic acid ester according to claim 1, wherein the silicon compound is selected from the group consisting of ethyl orthosilicate, silicon tetrachloride, water glass and sodium silicate; the titanium compound is selected from the group consisting of titanium sulfate, titanium oxysulfate, titanium nitrate, titanium tetrachloride and orthotitanate; and the basic compound is selected from the group consisting of ammonia, ammonium carbonate, ammonium bicarbonate, urea, alkali metal hydroxide and alkali metal carbonate.

13. The process for preparing a carboxylic acid ester according to claim 12, wherein the ratio of the amount (gram equivalent) of nitric acid or sulfuric acid to the amount (mol) of the silicon compound in the acidic solution is 1 to 20; and the amount of the titanium compound in the acidic solution is such that a ratio of titania in the prepared silica-titania catalyst is 5 to 40% by weight.

14. The process for preparing a carboxylic acid ester according to claim 13, further comprises carrying out an aging at a temperature of 20° to 110° C. after said adding of said acidic solution to said solution of a basic compound.

* * * * *